United States Patent
Huh

(10) Patent No.: US 8,659,509 B2
(45) Date of Patent: Feb. 25, 2014

(54) METHOD FOR CONTROLLING CARTRIDGE OF WELDING HELMET HAVING DISPLAY FUNCTION OF WELDING OPERATION TIME

(75) Inventor: Moon Young Huh, Seoul (KR)

(73) Assignee: Otos Wing Co., Ltd. (KR)

( * ) Notice: Subject to any disclaimer, the term of this patent is extended or adjusted under 35 U.S.C. 154(b) by 680 days.

(21) Appl. No.: 12/950,413

(22) Filed: Nov. 19, 2010

(65) Prior Publication Data
US 2011/0156989 A1 Jun. 30, 2011

(30) Foreign Application Priority Data
Dec. 24, 2009 (KR) ........................ 10-2009-0130322

(51) Int. Cl.
*G09G 5/00* (2006.01)
*G08B 21/00* (2006.01)
*G04B 47/00* (2006.01)

(52) U.S. Cl.
USPC .................. 345/7; 345/8; 345/9; 340/636.15; 368/10; 359/13; 359/630; 359/631; 359/632; 359/633; 348/E13.036

(58) Field of Classification Search
USPC .......... 345/7–9; 340/636.15; 368/10; 359/13, 359/630–633; 348/E13.036; 349/11
See application file for complete search history.

(56) References Cited

U.S. PATENT DOCUMENTS

| 5,533,206 A | 7/1996 | Petrie et al. |
| 5,727,127 A * | 3/1998 | Schulze Horn et al. ........ 706/52 |
| 6,070,264 A | 6/2000 | Hamilton et al. |
| 7,199,767 B2 * | 4/2007 | Spero ............................... 345/7 |

* cited by examiner

*Primary Examiner* — Alexander S Beck
*Assistant Examiner* — Jeffrey Steinberg
(74) *Attorney, Agent, or Firm* — Cantor Colburn LLP

(57) ABSTRACT

Disclosed is a method for controlling a cartridge of a welding helmet having a function to display a welding operation time, which can protect the welder's face from intense light generated during a welding or cutting operation and also, enable automated light transmittance adjustment and operation time setting on a per operation basis, enabling a welding operation to be more efficiently performed. In the method including welding operation, cutting operation, grinding operation and X-mode operation steps, which are automatically performed in sequence according to preset conditions and a light transmittance and operation time of a liquid crystal screen of the cartridge, a control unit calculates an operation time of the liquid crystal screen indicating how long the liquid crystal screen is kept dark, and the calculated operation time is stored in a memory unit so as to be displayed on a display unit in a life mode step.

4 Claims, 6 Drawing Sheets

METHOD FOR CONTROLLING CARTRIDGE OF WELDING HELMET HAVING DISPLAY FUNCTION OF WELDING OPERATION TIME

BACKGROUND OF THE INVENTION

1. Field of the Invention

The present invention relates to a method for controlling a cartridge of a welding helmet, and more particularly, to a method for controlling a cartridge of a welding helmet having a function to display a welding operation time, which can protect the welder's face from intense light generated during a welding or cutting operation and also, enable automated light transmittance adjustment and operation time setting on a per operation basis, enabling a welding operation to be performed more efficiently.

2. Description of the Related Art

Generally, arc welding is a technique to bond two metal pieces by locally heating and melting the metal pieces using fusibility of metals. As one of protective equipment, a welder should wear a welding helmet to protect their face from high heat, intense light and harmful gas generated during welding.

A conventional welding helmet having a handle piece, however, is troublesome in use since the welder has to repeatedly put on the welding helmet whenever they perform a welding operation.

As a result of continuous research and development for improving working efficiency of the welder, currently, a welding helmet using a band is commercialized.

The welding helmet, which serves as protective equipment for use in a welding or cutting operation, especially, has an anti-blinding device (hereinafter, referred to as a cartridge) for protecting the welder's eyes from intense light caused by sparks discharged during the welding or cutting operation.

Such a cartridge is attached to the welding helmet, and acts to intercept visible light having a wavelength of 780 nm or more and less than 365 nm while controlling transmission of visible light, thereby allowing the welder to view a welding operation without risking eye damage.

U.S. Pat. No. 5,533,206 discloses a welding helmet in which an Electronic Quick Change (EQC) cartridge including a Liquid Crystal Display (LCD) lens, a solar battery and a photo sensor cell is fixedly mounted in a cartridge housing located inside the welding helmet. The LCD lens is positioned directly in front of the welder's eyes, thereby functioning as an actual viewing window. The solar battery absorbs light and thus, functions as an energy input unit. The photo sensor cell detects sparks and other intense light and thus, acts as an input unit of a circuit that automatically adjusts a variable opaque degree of the LCD lens.

U.S. Pat. No. 6,070,264 discloses a welding helmet, which includes a shutter through which a wearer of the helmet may view a welding operation, an electronic controller coupled to the shutter to control a light transmittance of the shutter, a photo sensor to sense the intensity of light emanating from the welding operation, and an electronic circuit to allow the electronic controller to adjust the light transmittance of the shutter in response to the signal from the photo sensor.

However, the above-described conventional welding helmets have a problem in that the cartridge, which serves to sense the luminance of light emanating from the welding operation and to automatically drive the LCD lens or the shutter to a darker shade according to the luminance of light so as to protect the welder's eyes, has no functions of light transmittance adjustment and operation time setting on a per operation basis, causing difficulty in efficient implementation of the welding operation.

SUMMARY OF THE INVENTION

Therefore, the present invention has been made in view of the above problem, and it is an object of the present invention to provide a method for controlling a cartridge of a welding helmet having a function to display a welding operation time, which can protect the welder's face from intense light generated during a welding or cutting operation and also, enable automated light transmittance adjustment and operation time setting on a per operation basis, enabling a welding operation to be performed more efficiently.

In accordance with an aspect of the present invention, the above and other objects can be accomplished by the provision of a method for controlling a cartridge of a welding helmet having a function to display a welding operation time, the method including a welding operation step, a cutting operation step, a grinding operation step and an X-mode operation step, which are automatically performed in sequence according to preset conditions and a light transmittance and operation time of a liquid crystal screen of the cartridge, wherein a control unit calculates an operation time of the liquid crystal screen indicating how long the liquid crystal screen is kept dark, and the calculated operation time is stored in a memory unit so as to be displayed on a display unit in a life mode step.

The control unit senses a battery voltage may perform a low voltage alarm step if a low voltage is applied, and may display a low voltage state indicator on the display unit.

A 12 hour or 24 hour clock mode, Fahrenheit or Celsius, alarm time adjustment, and time adjustment may be selected in the life mode step, and if the alarm time adjustment is selected in the life mode step, an alarm time setting step may be performed to set hour and minute of an alarm time, and the setting of the alarm time may be completed once a welder pushes an ENTER key. Also, if the time adjustment is selected in the life mode step, a time adjustment step may be performed to set hour and minute of a time, and the setting of the time may be completed once the welder pushes the ENTER key.

The display unit may allow the welder to immediately view an operation time as soon as the life mode step begins to reduce power consumption.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, an exemplary embodiment of the present invention will be described in detail with reference to the accompanying drawings.

The terms or words used in the specification and claims of the present invention are not interpreted using typical or dictionary limited meanings, and are constructed as meanings and concepts conforming to the technical spirit of the present invention based on the principle that the inventors can appropriately define the concepts of the terms to explain the present invention in the best manner. Accordingly, it is to be understood that the detailed description, which will be disclosed along with the accompanying drawings, is intended to describe the exemplary embodiments of the present invention and is not intended to represent all technical ideas of the present invention. Therefore, it should be understood that various equivalents and modifications can exist which can replace the embodiments described in the time of the application. Also, the same reference numbers used throughout the drawings refer to the same or like parts.

Figure 1:
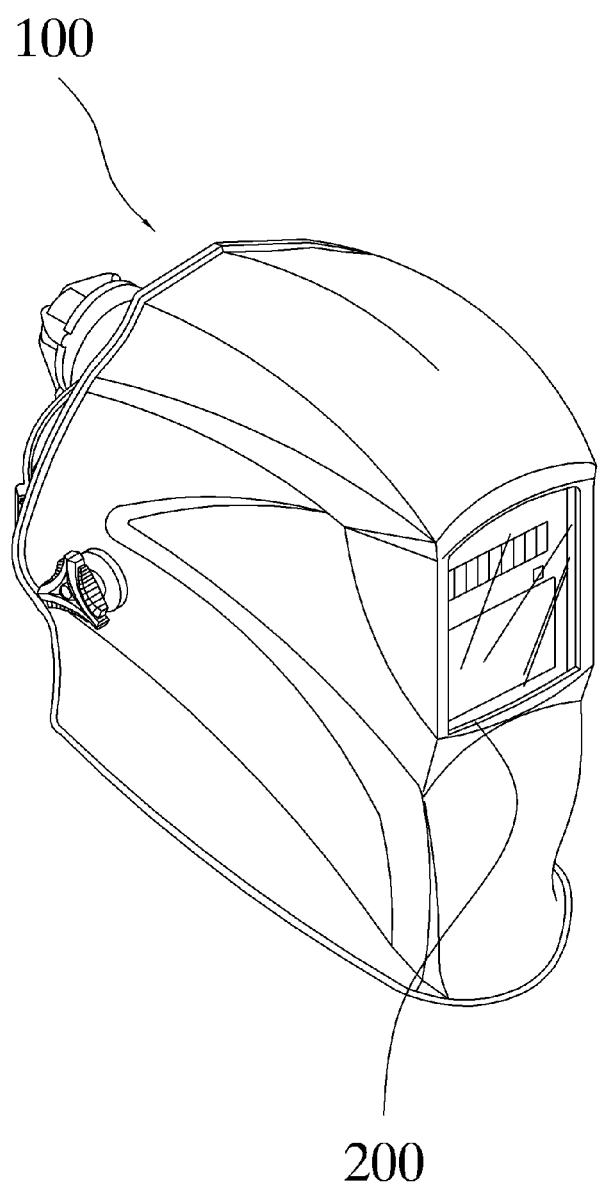
FIG. 1 is a perspective view illustrating a welding helmet according to the present invention.
Figure 2:
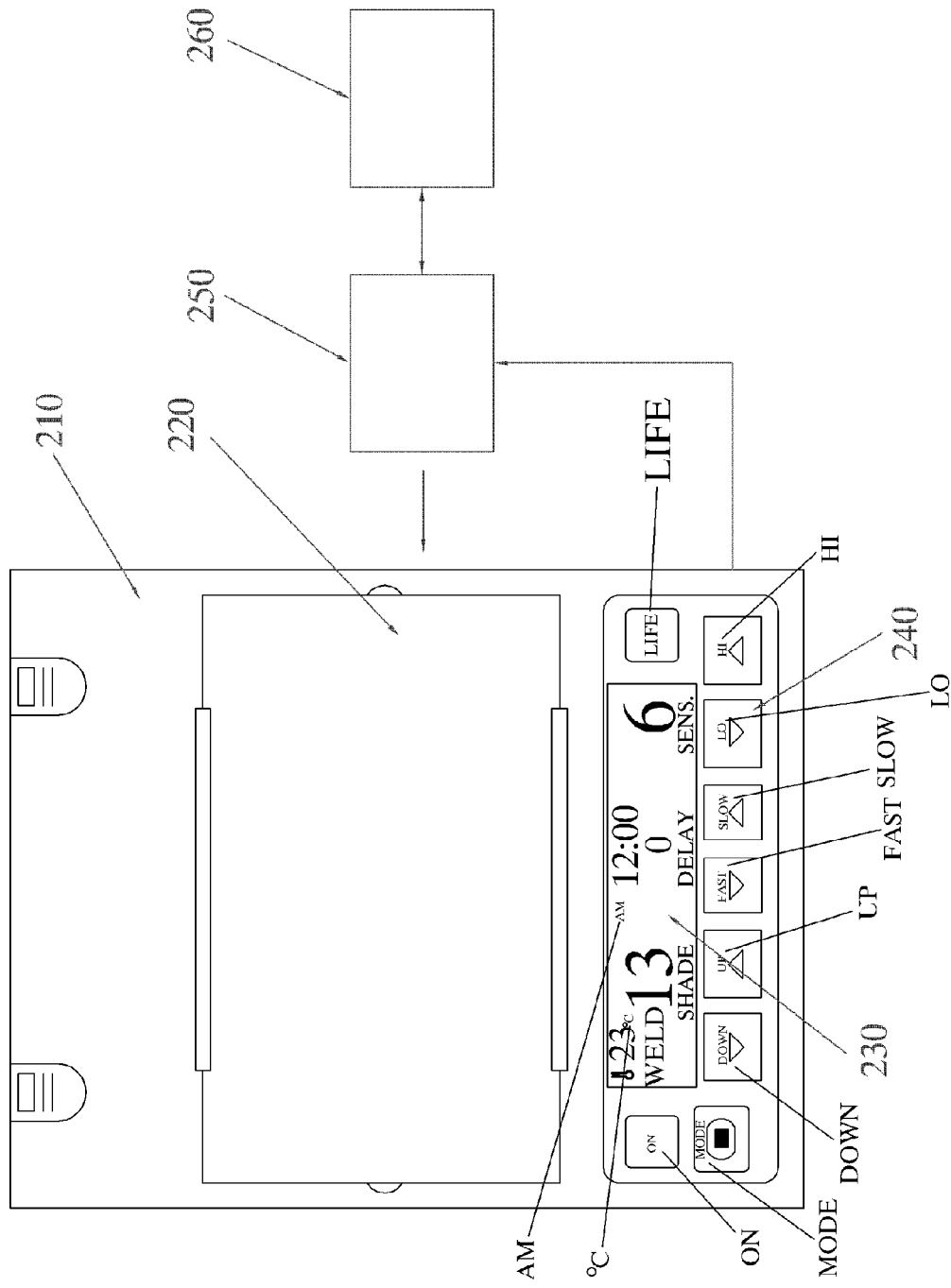
FIG. 2 is a detailed view of a cartridge illustrated in FIG. 1.

FIG. 1 is a perspective view illustrating a welding helmet according to the present invention, and FIG. 2 is a detailed view of a cartridge illustrated in FIG. 1.

As illustrated, the welding helmet 100 of the present invention is provided with a cartridge 200. The cartridge 200 includes a main body 210, a liquid crystal screen 220, a display unit 230, and a key input unit 240.

The welding helmet 100 is configured to cover and protect the welder's face, and the cartridge 200 is mounted at a front surface portion of the welding helmet 100.

The welding helmet 100 is preferably made of a lightweight material, such as incombustible plastic.

The main body 210 of the cartridge 200 defines an external appearance of the cartridge 200 and incorporates a control unit 250 and a memory unit 260 therein. The control unit 250 is typically a microcomputer.

The liquid crystal screen 220 has a variable light transmittance depending on a manual operation or control of the control unit 250. Accordingly, a welder who wears the welding helmet 100 to cover their face may perform a welding or cutting operation under the condition of an appropriate brightness by controlling the light transmittance of the liquid crystal screen 220.

The display unit 230 is used to display, e.g., a user input command or an operation mode of the welding helmet 100.

The key input unit 240 receives and transmits the input user command to the control unit 250.

The control unit 250 controls all operations of the welding helmet 100, and the memory unit 260 stores key input values and operation data values.

Hereinafter, the operation of the cartridge 200 provided in the welding helmet 100 having the above described configuration will be described in more detail.

Figure 3:
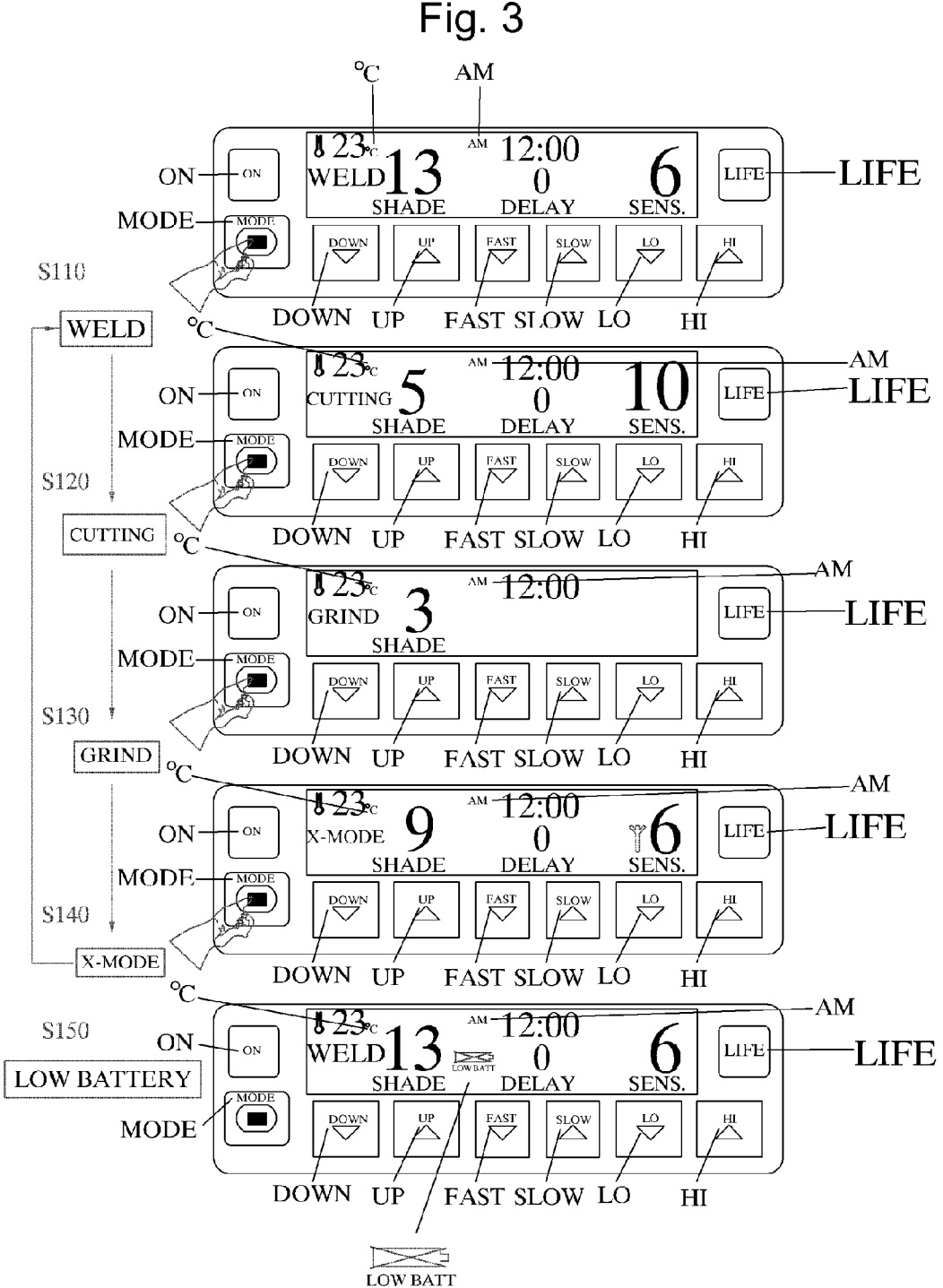
FIG. 3 is a view illustrating a method for controlling the cartridge of the welding helmet according to the present invention to adjust a light transmittance on a per operation basis.

FIG. 3 is a view illustrating a method for controlling the cartridge of the welding helmet according to the present invention to adjust a light transmittance on a per operation basis.

First, in the present invention, a welding operation step S110, a cutting operation step S120 a grinding operation step S130, and an X-mode operation step S140 may be automatically performed in sequence according to preset conditions and a light transmittance and operation time of the liquid crystal screen 220.

In this case, the control unit 250 may sense a battery voltage. For example, if a low voltage is applied, the control unit 250 may perform a low voltage alarm operation step S150 by activating a low voltage state indicator on the display unit 230.

Figure 4:
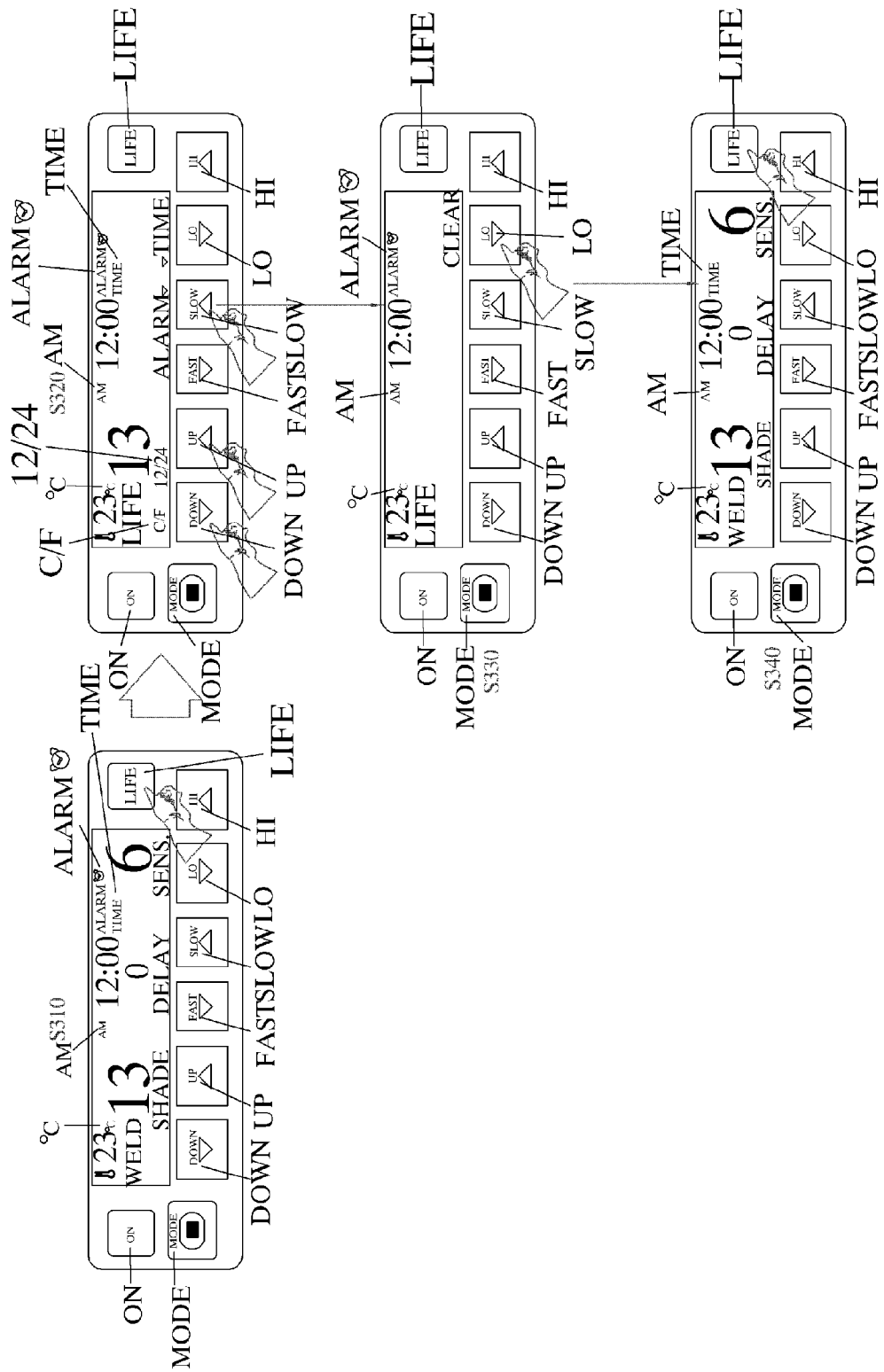
FIG. 4 is a view illustrating an operation time setting process according to the present invention.

FIG. 4 is a view illustrating an operation time setting process according to the present invention.

If the welder initially pushes a LIFE key (S210), a life mode step S220 follows.

In the life mode step S220, a 12 hour or 24 hour clock mode, Fahrenheit or Celsius, alarm time adjustment, and time adjustment may be selected.

In one example, if the alarm time adjustment is selected, a time setting step S230 is performed to set hour and minute of an alarm time. Then, if the welder pushes an ENTER key, the setting of the alarm time is completed (S240).

In another example, if the time adjustment is selected in the life mode step S220, a time adjustment step S250 is performed to set hour and minute of a desired time. Then, if the welder pushes the ENTER key, the setting of the desired time is completed (S260).

Figure 5:
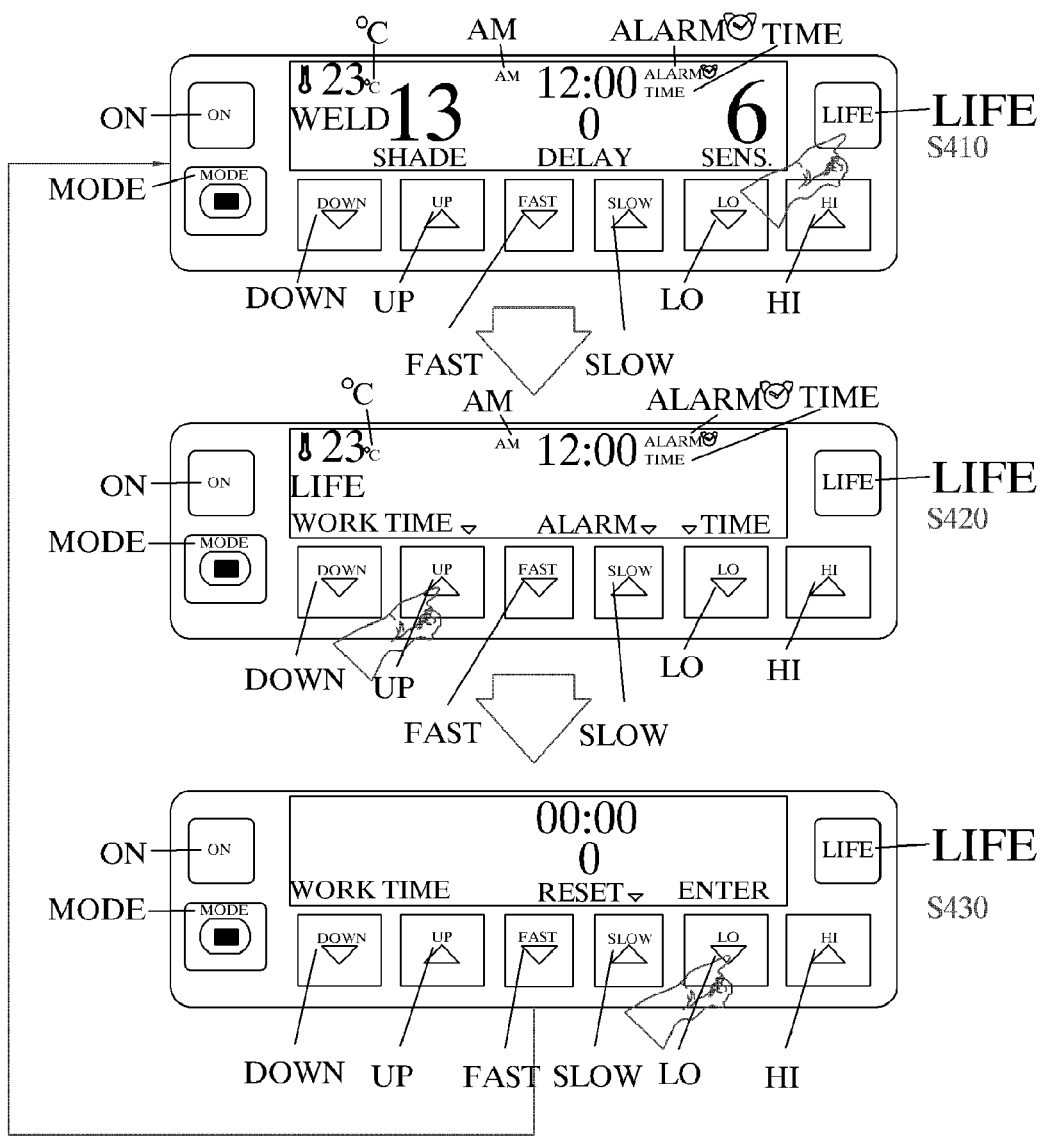
FIG. 5 is a view illustrating an alarm cancel process according to the present invention.

FIG. 5 is a view illustrating an alarm cancel process according to the present invention.

If the welder initially pushes the LIFE key (S310), an alarm adjustment step S320 follows.

In the alarm adjustment step S320, the welder is allowed to set an alarm adjustment mode. Then, if the welder selects a CLEAR key in an alarm cancel step S330, the cancel of the previously set alarm is completed (S340).

Figure 6:
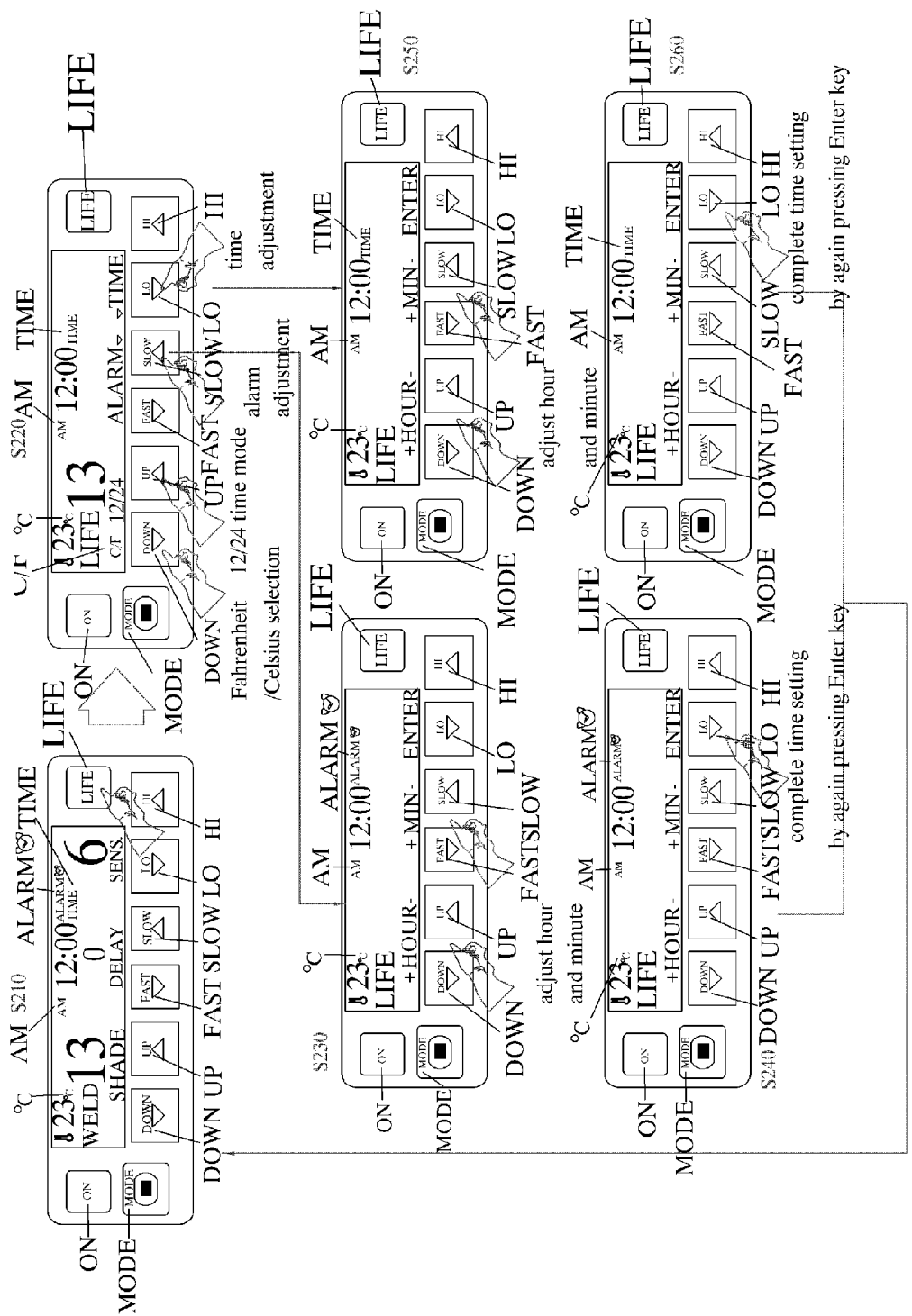
FIG. 6 is a view illustrating an operation time display process according to the present invention.

FIG. 6 is a view illustrating an operation time display process according to the present invention.

As illustrated, in the present invention, an operation time calculating step S410, an operation time setting step S420, and an operation time storing step S430 are performed in sequence.

In the operation time calculating step S410, the control unit 250 calculates an operation time indicating how long the liquid crystal screen 220 of the cartridge 200 is kept dark. The calculated operation time may be stored in the memory unit 260 and may be displayed on the display unit 230 in the life mode step S220.

The display unit 230 may display an operation time up to 99 hours and 60 minutes at maximum, and is reset when a battery is exchanged. For example, if the operation time reaches 99 hours and 60 minutes, and an alarm message is generated and operation time calculation is stopped. The display unit 230 may be reset only by the welder.

Preferably, the display unit 230 displays the operation time in minutes.

The display unit 230 may also display a temperature on the Fahrenheit or Celsius scale. The display unit 230 may display a fixed unit of a temperature on the Fahrenheit scale and a fixed operation time of 12 hours.

When the welder wants the operation time to be update in real time, for example, under the assumption that the display unit 230 is a Liquid Crystal Display (LCD), a temperature display region of the display unit 230 should be changed to a four digit region when in use, and the display unit should remain on at all times to change a data screen at the time when the liquid crystal screen 20 begins to transmit light. Thus, the display unit 230 may result in problematic power consumption.

The present invention may provide the display unit 230 with an optimum indicator arrangement to allow the welder to immediately view the operation time displayed on the display unit 230 as soon as the life mode step S220 begins.

In the present invention, operation times of the welding operation step S110, the cutting operation step S120, the grinding operation step S130 and the X-mode operation step S140 are calculated respectively and are displayed on the display unit 230 to allow the welder to rapidly identify the respective operation times.

In this case, an Off time of the liquid crystal screen 220 is controlled based on the luminance of light during the cutting operation step S120 and the grinding operation step S130. However, actually, the luminance of light may be significantly low, causing an error in the calculation of time. Therefore, in the present invention, a tolerance error range for calculation of the operation times of the cutting operation step S120 and the grinding operation step S130 may be expanded to eliminate the above described calculation error.

As is apparent from the above description, a method for controlling a cartridge of a welding helmet according to the present invention can not only protect the welder's face from intense light generated during a welding or cutting operation, but also enable automated light transmittance adjustment and operation time setting on a per operation basis, enabling a welding operation to be performed more efficiently.

The above description related to the preferred embodiments of the present invention and the accompanying drawings have been provided for illustrative purposes, and are not intended to limit the scope of the present invention defined by the claims. Thus, those skilled in the art will appreciate that various modifications, additions and substitutions are possible, without departing from the scope and spirit of the invention as disclosed in the accompanying claims. Accordingly, the technical protection range of the present invention should be determined by the appended claims.

What is claimed is:

1. A method for controlling a cartridge of a welding helmet having a function to display a welding operation time, the method comprising a welding operation step, a cutting operation step, a grinding operation step and an X-mode operation step, which are automatically performed in sequence according to preset conditions and a light transmittance and operation time of a liquid crystal screen of the cartridge,
   wherein a control unit calculates an operation time of the liquid crystal screen indicating how long the liquid crystal screen is kept dark, and the calculated operation time is stored in a memory unit so as to be displayed on a display unit in a life mode step.

2. The method according to claim 1, wherein the control unit senses a battery voltage, performs a low voltage alarm step if a low voltage is applied, and displays a low voltage state indicator on the display unit.

3. The method according to claim 1, wherein:
   a 12 hour or 24 hour clock mode, Fahrenheit or Celsius, alarm time adjustment, and time adjustment are selected in the life mode step;
   if the alarm time adjustment is selected in the life mode step, an alarm time setting step is performed to set hour and minute of an alarm time, and the setting of the alarm time is completed once a welder pushes an ENTER key; and
   if the time adjustment is selected in the life mode step, a time adjustment step is performed to set hour and minute of a time, and the setting of the time is completed once the welder pushes the ENTER key.

4. The method according to claim 1, wherein the display unit allows the welder to immediately view an operation time as soon as the life mode step begins to reduce power consumption.

* * * * *